US009629522B2

(12) United States Patent
Ando (10) Patent No.: US 9,629,522 B2
(45) Date of Patent: Apr. 25, 2017

(54) SEPARABLE MEDICAL INSTRUMENT, AND OPERATED SECTION AND OPERATING SECTION THEREOF

(71) Applicant: CANON KABUSHIKI KAISHA, Tokyo (JP)

(72) Inventor: Masahiro Ando, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 26 days.

(21) Appl. No.: 14/404,410

(22) PCT Filed: May 13, 2013

(86) PCT No.: PCT/JP2013/003034
§ 371 (c)(1),
(2) Date: Nov. 26, 2014

(87) PCT Pub. No.: WO2013/179586
PCT Pub. Date: Dec. 5, 2013

(65) Prior Publication Data
US 2015/0112143 A1    Apr. 23, 2015

(30) Foreign Application Priority Data

May 31, 2012  (JP) ................................. 2012-124501

(51) Int. Cl.
*A61B 1/00*         (2006.01)
*A61B 1/005*        (2006.01)
(Continued)

(52) U.S. Cl.
CPC .......... *A61B 1/0057* (2013.01); *A61B 1/0052* (2013.01); *A61B 1/00105* (2013.01);
(Continued)

(58) Field of Classification Search
CPC . A61B 1/0057; A61B 1/00105; A61B 1/0052; A61B 1/00128
See application file for complete search history.

(56) References Cited

U.S. PATENT DOCUMENTS

| 7,722,532 B2 | 5/2010 | Ikeda et al. | |
| 8,070,685 B2 * | 12/2011 | Harhen | A61B 8/12 600/146 |

(Continued)

FOREIGN PATENT DOCUMENTS

| JP | 2-161928 A | 6/1990 |
| JP | 5-20704 U | 3/1993 |

(Continued)

*Primary Examiner* — Timothy J Neal
(74) *Attorney, Agent, or Firm* — Canon U.S.A., Inc. IP Division (57) ABSTRACT

A medical instrument includes an operated section having a deformable portion and an operating section configured to deform the deformable portion. The operated section and the operating section are attachable to and detachable from each other. The operated section includes a wire 1 configured to penetrate the deformable portion. The operating section includes moving parts 11 to 13 configured to move the wire 1, and a connecting part 101 configured to contain the moving parts 11 to 13 movably and to be connected to the operated section. The moving parts 11 to 13 deform the deformable portion by moving the wire 1 with a connecting surface included in the connecting part 101 being disposed therebetween.

7 Claims, 6 Drawing Sheets (51) Int. Cl.
*A61B 1/04* (2006.01)
*A61B 17/00* (2006.01)

(52) U.S. Cl.
CPC .. *A61B 1/00128* (2013.01); *A61B 2017/0046* (2013.01); *A61B 2017/00314* (2013.01); *A61B 2017/00327* (2013.01)

(56) References Cited

U.S. PATENT DOCUMENTS

| | | | |
|---|---|---|---|
| 2006/0287576 A1* | 12/2006 | Tsuji | A61B 1/00105 600/132 |
| 2007/0232856 A1* | 10/2007 | Ueno | A61B 1/00039 600/118 |
| 2009/0149702 A1 | 6/2009 | Onoda et al. | |
| 2012/0100729 A1 | 4/2012 | Edidin et al. | |

FOREIGN PATENT DOCUMENTS

| | | |
|---|---|---|
| JP | 2000-014628 A | 1/2000 |
| JP | 2003-127085 A | 5/2003 |
| JP | 2005279253 A | 10/2005 |
| JP | 2009-160243 A | 7/2009 |
| JP | 2009-225876 A | 10/2009 |
| JP | 2010-194102 A | 9/2010 |
| WO | 20061059721 A1 | 6/2006 |
| WO | 2007/007873 A1 | 1/2007 |
| WO | 2009/035051 A | 3/2009 |

* cited by examiner

SEPARABLE MEDICAL INSTRUMENT, AND OPERATED SECTION AND OPERATING SECTION THEREOF

TECHNICAL FIELD

The present invention relates to a separable medical instrument in which an operated section and an operating section are attachable to and detachable from each other.

BACKGROUND ART

There is proposed a separable endoscope in which an insert section (operated section) and an operating section are attachable to and detachable from each other (PTL 1). This separable endoscope has an advantage that the operating section can be reused by changing only the insert section even when the insert section gets dirty.

There is also proposed an endoscope in which only an operation knob is removably provided (PTL 2). However, when an insert section in the endoscope of PTL 2 gets dirty, it is necessary to change all components except the operation knob.

CITATION LIST

Patent Literature

PTL 1: Japanese Patent Laid-Open No. 2010-194102
PTL 2: Japanese Patent Laid-Open No. 2009-160243

In the separable endoscope of PTL 1, a connecting part of the insert section or a connecting part of the operating section is not sealed. Therefore, liquid (for example, blood, cleaning liquid, or antiseptic solution) may infiltrate from the connecting part of the insert section or the connecting part of the operating section when the insert section is detached from the operating section. If the infiltrated liquid touches a power transmission member (for example, a wire, a pulley, or a gear) in the insert section or the operating section, durability of the power transmission member may be reduced.

SUMMARY OF INVENTION

The present invention provides a medical instrument that can suppress infiltration of liquid from a connecting part of an operated section or a connecting part of an operating section.

A medical instrument according to an aspect of the present invention includes an operated section having a deformable portion, and an operating section configured to deform the deformable portion. The operated section and the operating section are attachable to and detachable from each other. The operated section includes an operated-section-side wire configured to penetrate the deformable portion, and the operating section includes a moving part configured to move to move the wire, and an operating-section-side connecting part configured to contain the moving part movably and to be connected to the operated section. The moving part deforms the deformable portion by moving the wire with a connecting surface included in the operating-section-side connecting part being disposed therebetween.

Further features of the present invention will become apparent from the following description of exemplary embodiments with reference to the attached drawings.

DESCRIPTION OF EMBODIMENTS

Preferred embodiments of the present invention will be described in detail below with reference to the attached drawings. In the drawings, like components are denoted by like reference numerals, and redundant descriptions thereof are skipped.

First Embodiment

Figure 1:
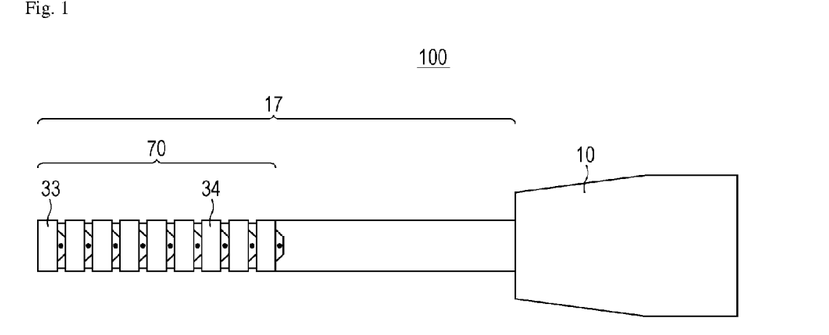
FIG. 1 is a side view of a medical instrument according to a first embodiment of the present invention.

FIG. 1 is a side view of a separable medical instrument 100 according to a first embodiment of the present invention. The medical instrument 100 includes an insert section (operated section) 17 and an operating section 10, and the insert section 17 and the operating section 10 are attachable to and detachable (separable) from each other. The insert section 17 includes a deformable portion 70 that bends and deforms, and the deformable portion 70 includes a distal end piece 33 and a plurality of intermediate pieces 34. An end of a wire (operated-section-side wire) is connected to the distal end piece 33, and the wire penetrates the intermediate pieces 34. By operating the operating section 10 to move (push and pull) the wire, the deformable portion 70 is bent and deformed.

FIGS. 2A to 2D are enlarged sectional views of connecting parts in the medical instrument 100 of the first embodiment.

The insert section 17 includes a wire (operated-section-side wire) 1, a magnet 3, a magnet 4, a rotating member 5, a magnet 6, a magnet 7, an elastic member (spring) 8, and a fixed portion 9. In the first embodiment, the wire 1 and a power transmission member (magnets 3 and 4) for transmitting power to the wire 1 are movably contained in a connecting part (operated-section-side connecting part) 171 of the insert section 17, and the connecting part 171 is sealed on an operating-section side so that the wire 1 and the magnets 3 and 4 are not exposed. This structure can suppress infiltration of liquid from the connecting part 171 of the insert section 17.

As described above, the wire 1 penetrates the intermediate pieces 34, and is connected at both ends to the distal end piece 33. Also, the wire 1 is wound around the rotating member 5. The magnets 3 and 4 (first magnet) are fixed to the wire 1. Therefore, when the magnets 3 and 4 move, the wire 1 also moves, and the rotating member 5 also moves (rotates). The rotating member 5 is formed by a pulley, and moves (rotates) along with movements of the wire 1 and the magnets 3 and 4. The magnets 6 and 7 are connected to a rotation shaft of the rotating member 5 via a member 67 or the like, and are movable with the rotating member 5 in a connecting direction X. The fixed portion 9 is fixed to a main body of the insert section 17. The elastic member 8 is provided between the rotation shaft of the rotating member 5 and the fixed portion 9, and pulls the rotating member 5 in a direction opposite to the connecting direction X.

The operating section 10 includes a magnet 11, a magnet 12, a wire (operating-section-side wire) 13, a magnet 15, a magnet 16, and a rotating member 31. The wire 13 and the magnets 15 and 16 constitute a moving part. In the first embodiment, the moving part is movably contained in a connecting part (operating-section-side connecting part) 101 of the operating section 10, and the connecting part 101 is sealed on an operated-section side so that the moving part is not exposed. This structure can suppress infiltration of liquid from the connecting part 101 of the operating section 10.

The magnets (second magnet) 11 and 12 are fixed to the wire 13. Since the magnet 11 and the magnet 4 have opposite polarities, they attract each other. While the magnet 4 serves as an S pole and the magnet 11 serves an N pole in FIGS. 2A to 2D, the poles may be reversed. Since the magnet 12 and the magnet 3 have opposite polarities, they attract each other. While the magnet 3 serves as an S pole and the magnet 12 serves as an N pole in FIGS. 2A to 2D, the poles may be reversed. The wire 13 is wound around the rotating member 31. The magnets 15 and 16 are fixed to a connecting surface of the operating section 10. Since the magnet 15 and the magnet 6 have opposite polarities, they attract each other. While the magnet 6 serves as an S pole and the magnet 15 serves as an N pole in FIGS. 2A to 2D, the poles may be reversed. Since the magnet 16 and the magnet 7 have opposite polarities, they attract each other. While the magnet 7 serves as an S pole and the magnet 16 serves as an N-pole in FIGS. 2A to 2D, the poles may be reversed. In this description, the connecting part of the insert section 17 refers to a part of the insert section 17 that is to be connected to the operating section 10 (connecting part of the operating section 10) and that is closest to the operating section 10. The connecting surface of the insert section 17 refers to a surface that is included in the connecting part of the insert section 17 and that is to be in contact with the operating section 10 (connecting surface of the operating section 10). The connecting part of the operating section 10 refers to a part of the operating section 10 that is to be connected to the insert section 17 (connecting part of the insert section 17) and that is closest to the insert section 17. The connecting surface of the operating section 10 refers to a surface that is included in the connecting part of the operating section 10 and that is to be in contact with the insert section 17 (connecting surface of the insert section 17). The rotating member 31 is formed by a pulley. By applying power in a rotating direction of the rotating member 31, the wire 13 is moved and the magnets 11 and 12 are moved in opposite directions.

Figure 2A:
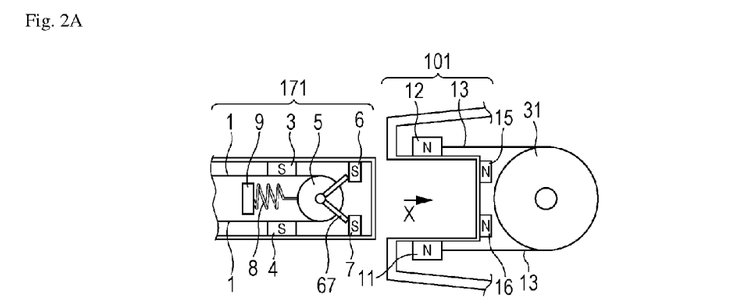
FIG. 2A is an enlarged sectional view of connecting parts in the medical instrument of the first embodiment.

FIG. 2A is a cross-sectional view illustrating a state in which the insert section 17 and the operating section 10 are separate from each other. In this state, the rotating member 5 is pulled by the elastic member 8, and therefore, is moved in the direction opposite to the connecting direction X. Therefore, in this state, the tension of the wire 1 is low, and the deformable portion 70 extends straight, as illustrated in FIG. 1. Also, the magnets 6 and 7 are moved in the direction opposite to the connecting direction X.

Figure 2B:
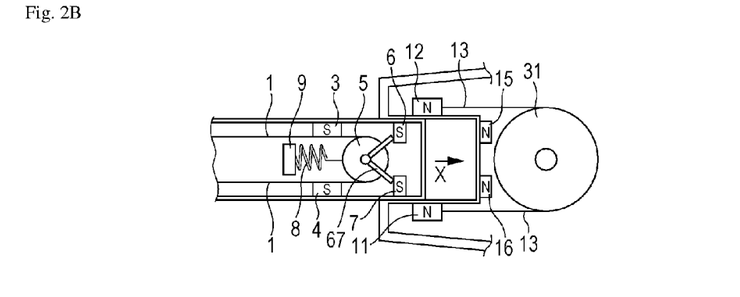
FIG. 2B is an enlarged sectional view of the connecting parts in the medical instrument of the first embodiment.
Figure 2C:
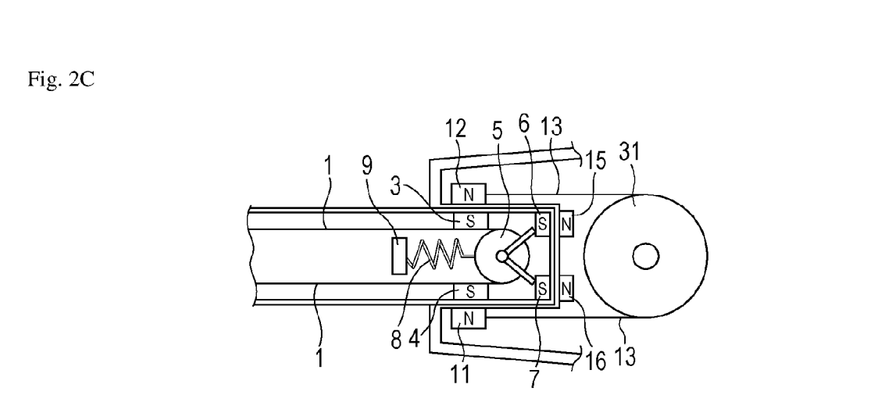
FIG. 2C is an enlarged sectional view of the connecting parts in the medical instrument of the first embodiment.

FIG. 2B is a cross-sectional view illustrating a state in which the insert section 17 and the operating section 10 are being connected. FIG. 2C is a cross-sectional view illustrating a state in which the insert section 17 and the operating section 10 are connected.

In the state of FIG. 2C, the magnets 6 and 7 and the magnets 15 and 16 attract each other, respectively, with the connecting surface of the insert section 17 and the connecting surface of the operating section 10 being disposed therebetween, so that the insert section 17 is fixed to the operating section 10. At this time, since the spring 8 expands, the magnets 6 and 7 and the rotating member 5 are moved in the connecting direction X. The magnets 6 and 7 are in contact with the connecting surface of the insert section 17. Since the rotating member 5 is moved in the connecting direction X, the wire 1 is tensioned. Further, in the state of FIG. 2C, the magnet 3 and the magnet 12 attract each other with the connecting surface of the insert section 17 and the connecting surface of the operating section 10 being disposed therebetween, and the magnet 4 and the magnet 11 also attract each other with the connecting surface of the insert section 17 and the connecting surface of the operating section 10 being disposed therebetween. Therefore, the magnet 3 moves along with movement of the magnet 12, and the magnet 4 moves along with movement of the magnet 11.

Figure 2D:
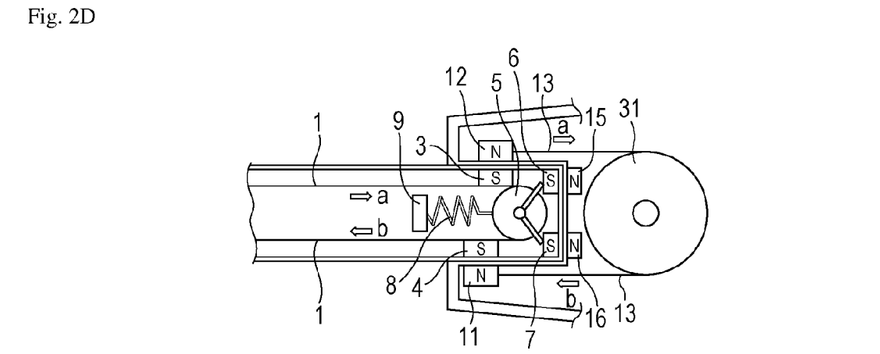
FIG. 2D is an enlarged sectional view of the connecting parts in the medical instrument of the first embodiment.

FIG. 2D is a cross-sectional view illustrating a state in which the wire 1 of the insert section 17 and the wire 13 of the operating section 10 are simultaneously moving while the insert section 17 and the operating section 10 are connected. By rotating the rotating member 31 in the rotating direction, the wire 13 is moved in directions of arrows a and b. When the wire 13 moves, the magnets 11 and 12 move, the magnets 3 and 4 also move, and the wire 1 moves in the directions of arrows a and b. By movement of the wire 1, the deformable portion 70 is deformed (bent), as illustrated in FIG. 3B. By rotating the rotating member 31 in a direction opposite to the direction of FIG. 2D, the deformable portion 70 can be deformed (bent), as illustrated in FIG. 3C.

Figure 3A:
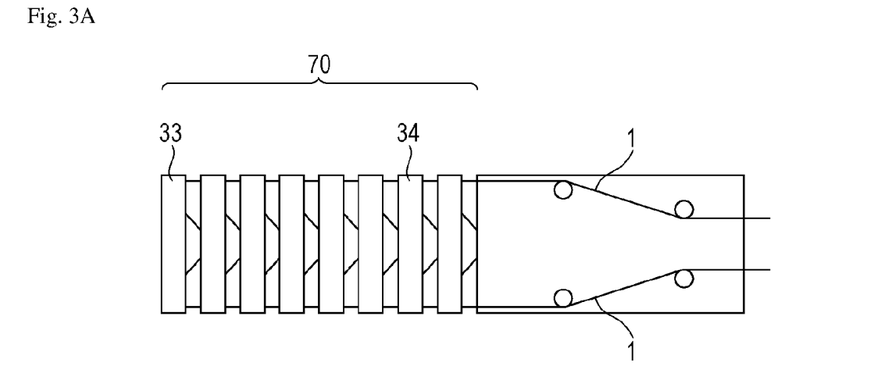
FIG. 3A is an enlarged sectional view of a deformable portion in the medical instrument of the first embodiment.
Figure 3B:
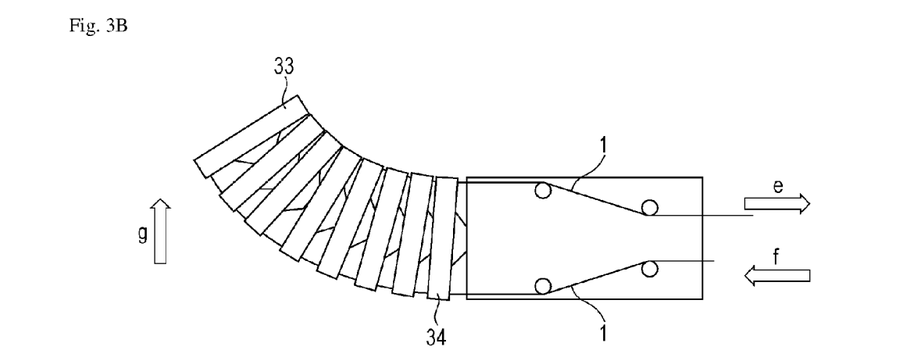
FIG. 3B is an enlarged sectional view of the deformable portion in the medical instrument of the first embodiment.
Figure 3C:
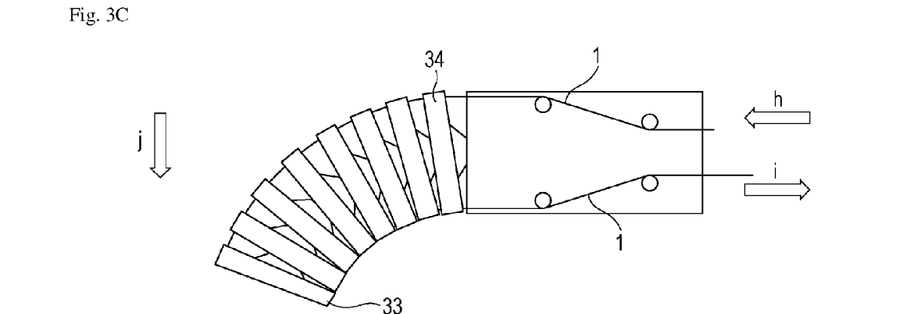
FIG. 3C is an enlarged sectional view of the deformable portion in the medical instrument of the first embodiment.

FIGS. 3A to 3C are enlarged sectional views of the deformable portion 70 and its surroundings in the insert section 17 of the first embodiment. FIG. 3A illustrates a state of the deformable portion 70 when the rotating member 31 is not rotated, FIG. 3B illustrates a state of the deformable portion 70 when the rotating member 31 is rotated, and FIG. 3C illustrates a state of the deformable portion 70 when the rotating member 31 is rotated in the direction opposite to the direction of FIG. 3B.

Referring to FIG. 3B, when the wire 1 moves in directions of arrows e and f, the distal end piece 33 bends in a direction of arrow g. Referring to FIG. 3C, when the wire 1 moves in directions of arrows h and i, the distal end piece 33 bends in a direction of arrow j.

Figure 4A:
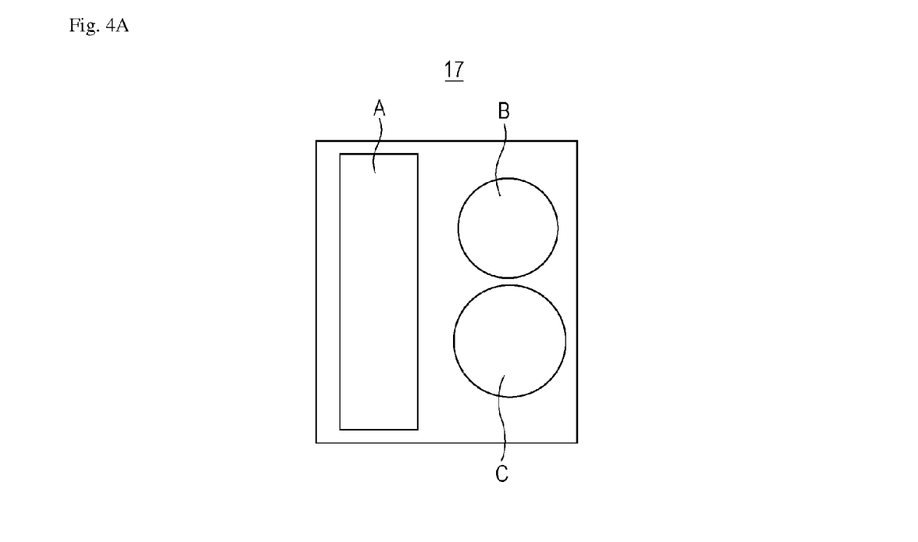
FIG. 4A is a cross-sectional view of an insert section in the medical instrument of the first embodiment.
Figure 4B:
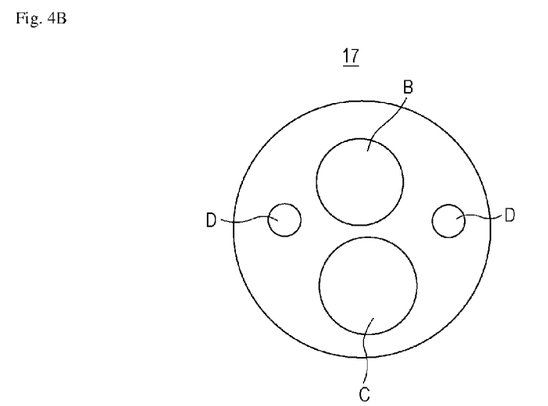
FIG. 4B is a cross-sectional view of the insert section in the medical instrument of the first embodiment.

FIGS. 4A and 4B are cross-sectional views of the insert section 17 taken along planes perpendicular to the connecting direction X. FIG. 4A is a cross-sectional view of the insert section 17 at the connecting part 171, and FIG. 4B is a cross-sectional view of the insert section 17 at the deformable portion 70. The rotating member, gears, the wire, etc. are provided in an area A, and an optical fiber, forceps, etc. are provided in areas B and C. Areas D correspond to holes through which the wire 1 extends.

According to the medical instrument 100 of the first embodiment, since the wire 1 is moved via the connecting surfaces of the insert section 17 and the operating section 10, for example, the connecting part of the insert section 17 and the connecting part of the operating section 10 can have a sealed structure.

While the wire 1 is moved via the connecting parts of both the insert section 17 and the operating section 10 in the first embodiment, it may be moved via the connecting part of any one of the insert section 17 and the operating section 10. In this case, for example, the connecting part of any one of the insert section 17 and the operating section 10 can have a sealed structure.

For example, when the insert section 17 is a disposable consumable article, only the operating section 10 preferably has a sealed structure. When it is necessary to clean only the insert section 17 without cleaning the operating section 10, the insert section 17 preferably has a sealed structure.

When the connecting part of the insert section 17 or the operating section 10 has a sealed structure, liquid is restricted from infiltrating into the section. Further, when the insert section 17 and the operating section 10 are carried in a separate state, for example, breakage of the wires can be prevented.

Second Embodiment

Next, a medical instrument 100A according to a second embodiment of the present invention will be described with reference to FIGS. 5A to 5D. FIGS. 5A to 5D are enlarged sectional views of connecting parts in the medical instrument 100A of the second embodiment.

The medical instrument 100A of the second embodiment includes an insert section (operated section) 17A and an operating section 10A. The insert section 17A and the operating section 10A are attachable to and detachable (separable) from each other. The insert section 17A includes a deformable portion 70A (not shown) that bends and deforms. By operating the operating section 10A to move (push and pull) wires 201 and 202, the deformable portion 70A is bent and deformed.

The insert section 17A includes the wires 201 and 202, magnets 18 and 19, lock bases 20 and 21, and lock claws 23 and 24. The magnets 18 and 19 are fixed to a connecting part (operated-section-side connecting part) 172 of the insert section 17A. The lock base 20 is contained in the connecting part 172 of the insert section 17A, and is fixed to the wire 201 and an elastic member 22. The lock base 21 is contained in the connecting part 172 of the insert section 17A, and is fixed to the wire 202 and the elastic member 22. The lock claw 23 is fixed to the lock base 20, and the lock claw 24 is fixed to the lock base 21. In the second embodiment, the wires 201 and 202 are movably contained in the connecting part 172, and the connecting part 172 is sealed on an operating-section side so that the wires 201 and 202 are not exposed. This structure can suppress infiltration of liquid from the connecting part 172 of the insert section 17A.

The operating section 10A includes a wire 13, lock bases 29 and 30, lock pins 27 and 28, and magnets 25 and 26. The magnets 25 and 26 are fixed to a connecting part (operating-section-side connecting part) 102 of the operating section 10A. The lock base 29 is fixed to the wire 13, and is also fixed to an elastic member 32. The lock base 30 is fixed to the wire 13, and is also fixed to the elastic member 32. The lock pin 27 is fixed to the lock base 29, and the lock pin 28 is fixed to the lock base 30. The wire 13 and the lock bases 29 and 30 constitute a moving part. In the second embodiment, the moving part is movably contained in the connecting part 102 of the operating section 10A, and the connecting part 102 is sealed on an operated-section side so that the moving part is not exposed. This structure can suppress infiltration of liquid from the connecting part 102 of the operating section 10A.

Figure 5A:
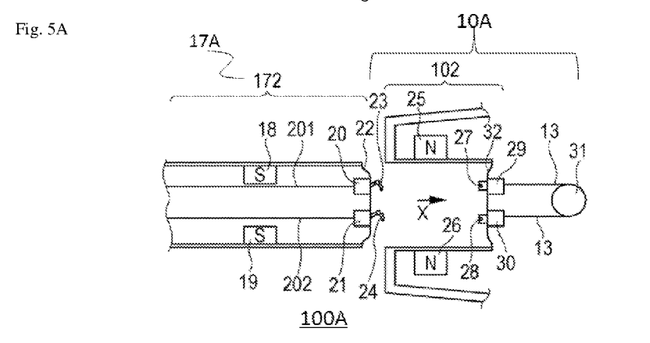
FIG. 5A is an enlarged sectional view of connecting parts in a medical instrument according to a second embodiment of the present invention.
Figure 5B:
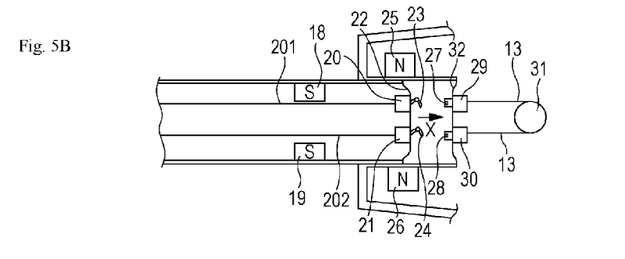
FIG. 5B is an enlarged sectional view of the connecting parts in the medical instrument of the second embodiment.

FIG. 5A is a cross-sectional view of the connecting parts in the medical instrument of the second embodiment, illustrating a state in which the insert section 17A and the operating section 10A are separate from each other. FIG. 5B is a cross-sectional view of the connecting parts, illustrating a state in which the insert section 17A and the operating section 10A are connected halfway.

Figure 5C:
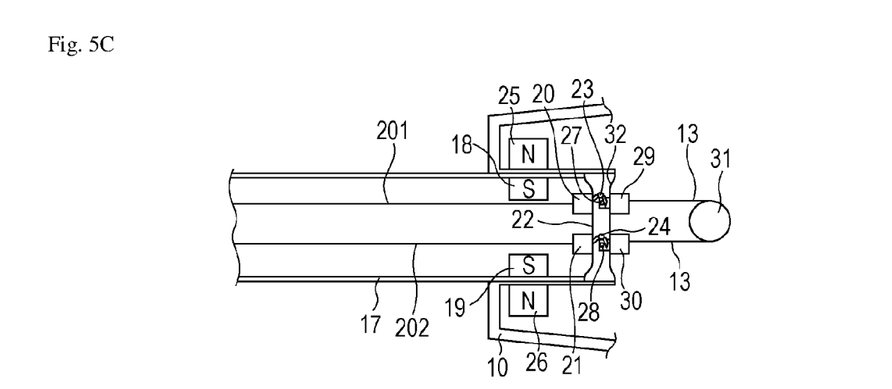
FIG. 5C is an enlarged sectional view of the connecting parts in the medical instrument of the second embodiment.

FIG. 5C is a cross-sectional view of the connecting parts, illustrating a state in which the insert section 17A and the operating section 10A are connected completely. The magnet 18 and the magnet 25 attract each other with the connecting surfaces being disposed therebetween, and are brought into tight contact with each other, and the magnet 19 and the magnet 26 attract each other with the connecting surfaces being disposed therebetween, and are brought into tight contact with each other, whereby the insert section 17A is fixed to the operating section 10A. The lock claw 23 passes over the lock pin 27 and is locked and the lock claw 24 passes over the lock pin 28 and is locked. Thus, the wire 13 and the wire 201 are connected, and similarly, the wire 13 and the wire 202 are connected. The elastic member 22 and the elastic member 32 are formed by members like rubber films, and expand and contract somewhat.

Figure 5D:
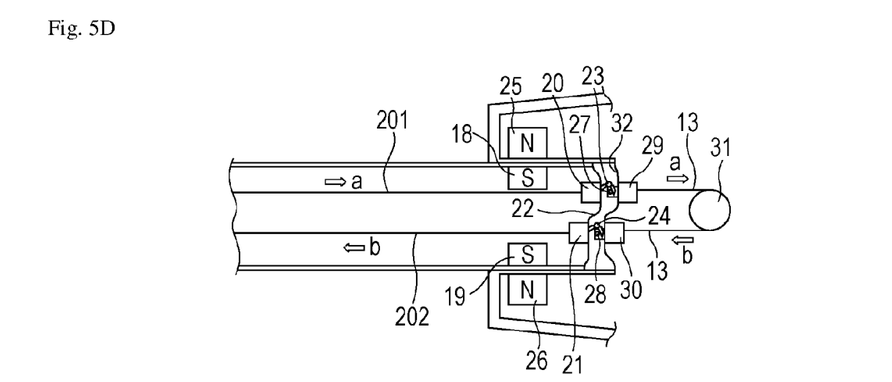
FIG. 5D is an enlarged sectional view of the connecting parts in the medical instrument of the second embodiment.

FIG. 5D is a cross-sectional view of the connecting parts, illustrating a state in which the wires 201 and 202 in the insert section 17A and the wire 13 in the operating section 10A are moving simultaneously. When the wire 13 moves in a direction or arrow a, the lock base 29 also moves in the direction of arrow a, the lock claw 23 caught by the lock pin 27 fixed to the lock base 29 also moves in the direction of arrow a, and the lock base 20 moves similarly. Thus, the wire 201 also moves in the direction of arrow a. At this time, the elastic member 32 and the elastic member 22 deform to expand or contract. Similarly, when the wire 13 moves in a direction of arrow b, the lock base 30 similarly moves in the direction of arrow b, the lock claw 24 caught by the lock pin 28 fixed to the lock base 30 moves in the direction of arrow b, and the lock base 21 moves similarly. Thus, the wire 202 also moves in the direction of arrow b. At this time, the elastic member 32 and the elastic member 22 deform to expand or contract. The wire 13 can be turned by the rotating member 31. The lock claws 23 and 24 are formed by dogleg hooks, and are biased in a clockwise direction by unillustrated torsion springs. For locking, the dogleg lock claws 23 and 24 pass over the pins. For unlocking, the lock claws 23 and 24 are biased in a counterclockwise direction, and turn in the counterclockwise direction to be disengaged from the lock pins 27 and 28.

Since the structures (for example, the deformable portion 70A) of the medical instrument 100A of the second embodiment are similar to those adopted in the medical instrument 100 of the first embodiment except for the structures illustrated in FIGS. 5A to 5D, descriptions thereof are skipped.

According to the medical instrument 100A of the second embodiment, since the wires 201 and 202 are moved via the connecting surfaces (elastic members) 22 and 32 of the insert section 17A and the operating section 10A, respectively, for example, the connecting part 172 of the insert section 17A and the connecting part 102 of the operating section 10A can have a sealed structure.

While the wires 201 and 202 are moved via the connecting parts of both the insert section 17A and the operating section 10A in the second embodiment, they may be moved via the connecting part of any one of the insert section 17A and the operating section 10A. In this case, for example, the connecting part of any one of the insert section 17A and the operating section 10A can have a sealed structure.

When the connecting part of the insert section 17A or the operating section 10A has a sealed structure, infiltration of liquid into the section can be suppressed. Further, when the insert section 17A and the operating section 10A are carried in a separate state, for example, breakage of the wires can be prevented.

Since the operated-section-side wire and the operating-section-side wire are connected with the connecting surface of the operated-section-side connecting part and the connecting surface of the operating-section-side connecting part being disposed therebetween in the medical instrument of the second embodiment, power can be more easily transmitted from the operating section to the operated section than in the first embodiment.

Third Embodiment

Figure 6A:
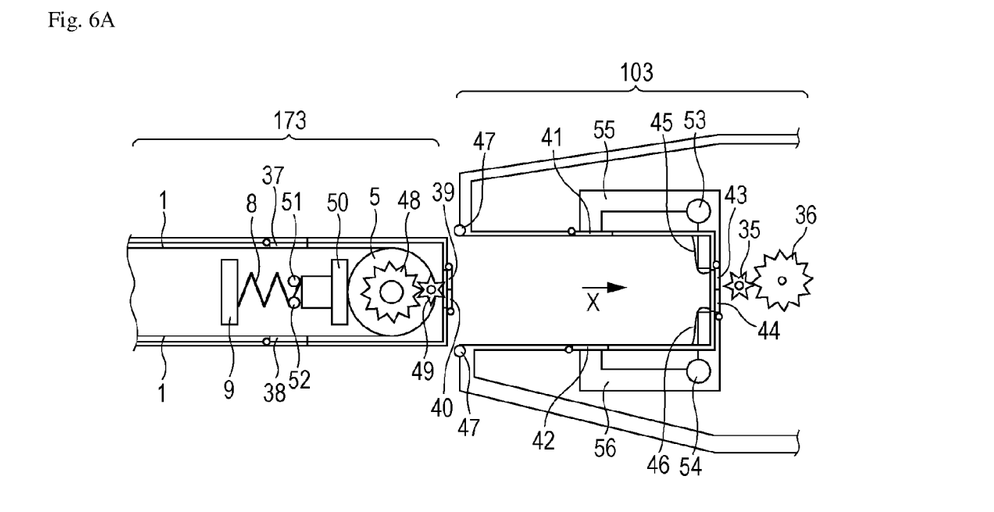
FIG. 6A is an enlarged sectional view of connecting parts in a medical instrument according to a third embodiment of the present invention.
Figure 6B:
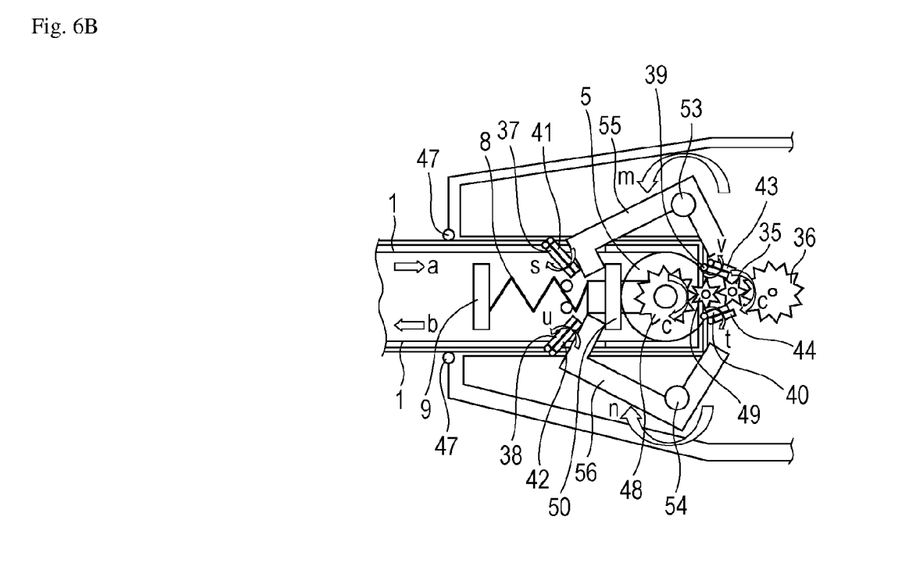
FIG. 6B is an enlarged sectional view of the connecting parts in the medical instrument of the third embodiment.

Next, a medical instrument according to a third embodiment of the present invention will be described with reference to FIGS. 6A and 6B. FIGS. 6A and 6B are cross-sectional views of connecting parts in the medical instrument of the third embodiment.

A medical instrument 100B of the third embodiment includes an insert section (operated section) 17B and an operating section 10B, and the insert section 17B and the operating section 10B are attachable to and detachable (separable) from each other. The insert section 17B includes a deformable portion 70B that bends and deforms. By operating the operating section 10B to move (push or pull) a wire 1, the deformable portion 70B is bent and deformed.

The insert section 17B includes the wire 1, a rotating member 5, a gear 48, a gear 49, an elastic member 8, a fixed portion 9, a moving base 50, lids 37 and 38, lids 39 and 40, and stoppers 51 and 52.

The wire 1 is contained in a connecting part of the insert section 17B, and is wound around the rotating member 5. The gear 48 is fixed to the rotating member 5. The moving base 50 is connected to the elastic member 8, and can move the rotating member 5, the gear 48, and the gear 49. The gear 48 and the gear 49 are meshed with each other, and rotate to transmit power to the wire 1. The gear 48 and the gear 49 correspond to an operated-section-side power transmission member. The lids 37 and 38 and the lids 39 and 40 are each sealed with an O-ring and a spring that are not illustrated. The lids 39 and 40 are closed when the insert section 17B and the operating section 10B are separate from each other, and are open when the insert section 17B and the operating section 10B are connected to each other. The lids 39 and 40 correspond to an operated-section-side opening and closing portion.

The operating section 10B includes a lever 55, a lever 56, a gear 35, a gear 36, lids 41 and 42, lids 43 and 44, rubber sheets 45 and 46, and an O-ring 47.

The lever 55 is turnable about a pivot 53. The lever 56 is turnable about a pivot 54. The gear 35 and the gear 36 are meshed with each other, and rotate to transmit power from an unillustrated power source to the gear 49. The gear 35 and the gear 36 correspond to an operating-section-side power transmission member. The lids 41 and 42 and the lids 43 and 44 are each sealed with an O-ring and a spring that are unillustrated. The lids 43 and 44 are closed when the insert section 17B and the operating section 10B are separate, and are open when the insert section 17B and the operating section 10B are connected. The lids 43 and 44 correspond to an operating-section-side opening and closing portion. The rubber sheets 45 and 46 are elastic and deformable members.

FIG. 6A is a cross-sectional view of the connecting parts in the medical instrument of the third embodiment, illustrating a state in which the insert section 17B and the operating section 10B are separate from each other. FIG. 6B is a cross-sectional view of the connecting parts in the medical instrument of the third embodiment, illustrating a state in which the insert section 17B and the operating section 10B are connected and the gear 36 in the operating section 10B and the wire 1 in the insert section 17B are moving simultaneously.

When the insert section 17B is connected to the operating section 10B, the levers 55 and 56 turn to push the moving base 50. When the moving base 50 is pushed, the gears 48 and 49 are moved in a connecting direction X to be meshed with the gear 35. At this time, the lid 37 and the lid 41 are pushed open by the lever 55, and the lid 38 and the lid 42 are pushed open by the lever 56. When the gear 49 moves in the connecting direction X, the lids 39 and 40 and the lids 43 and 44 are opened. The rubber sheets 45 and 46 deform when the levers 55 and 56 are pushed by the insert section 17B. The rubber sheets 45 and 46 seal the connecting part of the operating section 10B both when the insert section 17B and the operating section 10B are separate and when the insert section 17B and the operating section 10B are connected.

When the insert section 17B is connected to the operating section 10B, the lids 37 and 41 open in a direction of arrow s, the lids 38 and 42 open in a direction of arrow u, the lids 39 and 43 open in a direction of arrow v, and the lids 40 and 44 open in a direction of arrow t. At this time, the lever 55 turns in a direction of arrow m, and the lever 56 turns in a direction of arrow n.

By rotating the gear 35 in a direction of arrow c, the gear 48 is rotated in the direction of arrow c, and the wire 1 is moved in directions of arrow a and b. By moving the wire 1, the deformable portion 70B can be deformed similarly to the other embodiments. When the insert section 17B and the operating section 10B are connected, the O-ring 47 seals the insert section 17B and the operating section 10B so that liquid does not infiltrate into a gap therebetween.

Since the structures (for example, the deformable portion 70B) of the medical instrument 100B of the third embodiment are similar to those adopted in the medical instrument 100 of the first embodiment except for the structures illustrated in FIGS. 6A and 6B, descriptions thereof are skipped.

According to the medical instrument 100B of the third embodiment, when the insert section 17B and the operating section 10B are connected, the medical instrument 100B can have a sealed structure. Further, when the insert section 17B and the operating section 10B are separated, the operating-section side of the insert section 17B and the insert-section side of the operating section 10B are sealed. That is, when the insert section 17B and the operating section 10B are separate from each other, a connecting part 173 of the insert section 17B contains the operated-section-side power transmission member, and a connecting part 103 of the operating section 10B contains the operating-section-side power transmission member. Therefore, in the medical instrument 100B of the third embodiment, infiltration of liquid into the insert section 17B or the operating section 10B can be suppressed both when the insert section 17B and the operating section 10B are connected and when the insert section 17B and the operating section 10B are separate.

According to the medical instrument 100B of the third embodiment, the insert section 17B and the operating section 10B have the opening and closing portions, and are connected by the opening and closing portions. Therefore, according to the medical instrument 100B of the third embodiment, for example, the connecting part 173 of the insert section 17B and the connecting part 103 of the operating section 10B can be sealed when the insert section 17B and the operating section 10B are separate.

While both the insert section 17B and the operating section 10B have the opening and closing portions in the third embodiment, any one of the insert section 17B and the operating section 10B may have an opening and closing portion. In this case, for example, the connecting part of any one of the insert section 17B and the operating section 10B can be sealed when the insert section 17B and the operating section 10B are separate.

By sealing the connecting part of the insert section 17B or the operating section 10B, infiltration of liquid into the section can be suppressed. Further, when the insert section 17B and the operating section 10B are carried in a separate state, for example, breakage of the wires can be prevented.

In the medical instrument of the third embodiment, since the operated-section-side power transmission member and the operating-section-side power transmission member are directly connected, power can be more easily transmitted from the operating section to the operated section than in the first and second embodiments.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-124501, filed May 31, 2012, which is hereby incorporated by reference herein in its entirety.

The invention claimed is:

1. A medical instrument comprising:
an operated section having a deformable portion; and
an operating section configured to deform the deformable portion,
wherein the operated section and the operating section are attachable to and detachable from each other,
wherein the operated section includes an operated-section-side wire configured to penetrate the deformable portion, and a first magnet coupled to the operated-section-side wire,
wherein the operating section contains therein
a moving part that in accordance with its movement moves the operated-section-side-wire and that includes a second magnet configured to attract the first magnet, and
wherein the operating section contains the moving part movably and sealed without being exposed to an exterior and to be coupled to the operated section, and
wherein the moving part deforms the deformable portion by moving the operated-section-side wire by moving the first magnet using the second magnet.

2. The medical instrument according to claim 1,
wherein the moving part includes a rotating member and an operating-section-side wire wound around the rotating member.

3. The medical instrument according to claim 2,
wherein the second magnet is provided on the operating-section-side wire.

4. The medical instrument according to claim 2,
wherein the operated-section-side wire and the operating-section-side wire are connected with the connecting surface of the operated-section-side connecting part and the connecting surface of the operating-section-side connecting part being disposed therebetween.

5. The medical instrument according to claim 1, wherein the operating section comprises a depressed portion to which the operated section is inserted.

6. The medical instrument according to claim 5, wherein the second magnet is configured to move along a sidewall of the depressed portion.

7. An operated section of a medical instrument including the operated section and an operating section that are attachable to and detachable from each other, the operated section comprising:
a deformable portion;
a wire configured to penetrate the deformable portion; and
a first magnet coupled to the wire, wherein the wire is configured to move by moving the first magnet by a magnetic attracting force by a second magnet included in the operating section, further wherein the first magnet and the wire are sealed so as not to be exposed to an exterior.

* * * * *